(12) United States Patent  
Yang et al.

(10) Patent No.: US 9,090,864 B2
(45) Date of Patent: Jul. 28, 2015

(54) MULTI-TUBE BIOFILTER SYSTEM FOR TREATING WASTE GAS

(75) Inventors: Chunping Yang, Hunan (CN); Haining Yang, Hunan (CN); Hong Chen, Hunan (CN); Guanlong Yu, Hunan (CN); Guangming Zeng, Hunan (CN); Shenglian Luo, Hunan (CN)

(73) Assignee: Chunping Yang, Changsha, Hunan (CN)

( * ) Notice: Subject to any disclaimer, the term of this patent is extended or adjusted under 35 U.S.C. 154(b) by 158 days.

(21) Appl. No.: 13/814,240

(22) PCT Filed: Jul. 27, 2011

(86) PCT No.: PCT/CN2011/077658
§ 371 (c)(1),
(2), (4) Date: Feb. 4, 2013

(87) PCT Pub. No.: WO2012/016494
PCT Pub. Date: Feb. 9, 2012

(65) Prior Publication Data
US 2013/0137170 A1    May 30, 2013

(30) Foreign Application Priority Data
Aug. 5, 2010  (CN) .......................... 2010 1 0245866

(51) Int. Cl.
*C12M 1/00*    (2006.01)
*C12M 1/12*    (2006.01)
*B01D 53/85*   (2006.01)

(52) U.S. Cl.
CPC .............. *C12M 25/14* (2013.01); *B01D 53/85* (2013.01); *B01D 2257/708* (2013.01)

(58) Field of Classification Search
CPC .. C12M 25/14; B01D 53/85; B01D 2257/708
USPC .......................................... 435/289.1
See application file for complete search history.

(56) References Cited

U.S. PATENT DOCUMENTS 6,271,020 B1 * 8/2001 Coleman .................... 435/299.1
7,311,743 B2 * 12/2007 Deshusses ................. 435/289.1
(Continued)

FOREIGN PATENT DOCUMENTS

CN        101264422 A  *  9/2008
GB        1348161      *  4/1970

OTHER PUBLICATIONS

CN101264422A machine translation (Sep. 2008).*

*Primary Examiner* — Nathan Bowers
*Assistant Examiner* — Timothy Barlow
(74) *Attorney, Agent, or Firm* — Raymond Y. Chan; David and Raymond Patent Firm

(57) ABSTRACT

Disclosed is a multi-tube biofilter system for treating waste gas. The multi-tube biofilter system includes a multi-tube biofilter and a nutrient solution supply system. The multi-tube biofilter includes an outer casing, at least two reticulated tubes disposed in the outer casing, a packing medium portion, and a nutrient solution spraying system. The outer casing is opened to define a gas inlet, a gas outlet, and a water outlet therein. The packing medium portion is attached to an outer surface of each of the reticulated tubes, wherein a liquid entering end of the nutrient solution spraying system is in communication with the nutrient solution supply system via a pipeline, and solution spraying ends of the nutrient solution spraying system face the reticulated tubes.

7 Claims, 4 Drawing Sheets

(56) References Cited

U.S. PATENT DOCUMENTS

| | | | |
|---|---|---|---|
| 2001/0053546 A1* | 12/2001 | Stewart et al. | 435/290.1 |
| 2003/0232428 A1* | 12/2003 | Daly | 435/299.1 |
| 2006/0027099 A1* | 2/2006 | Kim | 95/187 |
| 2010/0086436 A1* | 4/2010 | Roseberry et al. | 422/4 |
| 2010/0129895 A1* | 5/2010 | Crawford | 435/283.1 |

* cited by examiner

MULTI-TUBE BIOFILTER SYSTEM FOR TREATING WASTE GAS

BACKGROUND OF THE PRESENT INVENTION

1. Field of Invention

The present invention relates to the field of treatment devices for low concentration waste gas, and more particular to a biofilter system for treating malodorous or low concentration organic waste gas.

2. Description of Related Arts

In the recent years of industrial production, the consumption of organic fuel has been dramatically increased, which relatively produces large amount of malodorous gases and volatile organic compounds (VOCs). These VOCs not only increases in volume and variety, but also emits in different sites. Most of these VOCs are characterized with a pungent smell, and are the cause of adverse environmental damage such as atmospheric pollution, crop failures, and the destruction of the forest, in addition to being harmful to humans. It is no wonder why VOCs have aroused a widespread concern.

There are a number of technologies for controlling these malodorous gases or VOCs, such as absorption, adsorption, incineration, condensation, and biological methods. Relatively, the biological method for treating malodorous gases or VOCs has several advantages such as being cost-effective, environmentally friendly, adaptable to a wide range of applications, and low operation cost. With the aforementioned advantages of biological methods for treating low-concentration and high flow waste gases which contain biologically biodegradable VOCs it is no wonder why it is considered one of the best methods. Gas bio-filtration is a method of gas biological filtration technology achieving the goal of purifying VOCs by oxidizing the VOCs, wherein the microorganisms attached to the packing medium play a dominant role.

When the waste gas containing low concentration of VOCs passes through the gas biological filtering reactor, its gaseous pollutants are transferred into a biofilm, and then degraded and decomposed into biomass and inorganic substances, such as $CO_2$ and $H_2O$, by microorganisms (enzymes).

Recently, there are mainly two types of biofilters for treating malodorous gases or VOCs, i.e. conventional biofilters and biotrickling filters. The conventional biofilter comprises a biofilter medium bed (biologically active packing medium layer), a gravel layer, and a multi-tube distributing pipeline. The biofilter medium bed is filled with a biologically active medium, such as soil, peat, sawdust, or chaff, exists microorganisms which are able to degrade pollutants, and the waste gas is purified when it passes through the packing medium layer. The biofilter medium bed has several advantages, such as short residence time, high removal efficiency, simple device and low investment and operation costs. However, it has following disadvantages, such as large footprint, uneven air distribution, and unstable performance over a long operation duration. Special difficulties associated with this process are medium bed clogging, increased drop of pressure and deterioration in the removal caused by high degree of clogging when the conventional biofilter has been run for a long time.

The biotrickling filter is also known as a trickling filter bed. It utilizes inert raw materials for the packing medium such as crushed stones, plastic particles, ceramic and carbon fibers, wherein the circulating nutrient solution sprays from top to bottom to seed and cultivate biofilms on the surface of the packing medium. The biofilm has capabilities of adsorption and bio-degradation such that the gaseous pollutants are transferred into the biofilm and degraded. Generally, it is necessary to periodically supply nutrients necessary for microorganisms to maintain long-term stable removal efficiency. Compared with the conventional biofilter, the reaction conditions of the biotrickling filter are easy to control, the concentration of microorganisms is high per unit volume of medium bed, the waste gas doesn't have to be moistened, and it can be supplied with a concurrent flow or countercurrent flow to drop filtrate flow for the biotrickling filter. Whereas, the biotrickling filter has several disadvantages, such as medium clogging resulted by excess accumulation of microorganisms in the medium bed, an increased drop of pressure caused by generation of channeling flows, and consequent decrease of performance due to excess biomass accumulation when the biotrickling filter is operated at especially under high load for a long period of time.

Existing biofilters employing gas biofiltration technology have several disadvantages: its medium bed are relatively high, its volume load is relatively low, its handling capacity is relatively small, its gas distribution is uneven, its drop of pressure is relatively large, and its packing medium bed is easy to clog. Practitioners have developed a tubular gas biofilter system which is comprised of a thin tubular layer of inert packing medium fixed in a cylindrical casing by a simple supporting means so that the cylindrical casing is divided into an outer gas chamber and an inner gas chamber. The waste gas passes through the packing medium from inside to outside or vice versa so as to degrade pollutants thereof. The nutrient solution sprays from top to bottom to supply the biofilm in the packing medium portion with nutrients. The tubular gas biofilter system definitely solves certain disadvantages of conventional biofilters and biotrickling filters, and has several advantages, such as its drop of pressure is relatively small, its height of bed layer is relatively low, its load per unit volume is high, its handling capacity is large and its operation cost is low. But tubular gas biofilters still have several disadvantages: the packing medium per unit volume of the reactor has a small surface such that its degradation efficiency is easily impacted by concentration of pollutants of the inlet gas, it has a weak shock resistance, and it has an unstable long-term performance of operation.

SUMMARY OF THE PRESENT INVENTION

The technical problems to be solved by the present invention are as follows: in response to the technical problems in the prior art, the present invention is to provide a simple, compact, low cost, and easy to operate and maintain multi-tube biofilter system for treating waste gas that has a large surface area per unit volume of the medium layer of the reactor, even distribution of gas flows and the biofilms, good removal efficiency, high shock load resistance, and stable performance for long-term operation.

To solve the above technical problems, the present invention employs the following technical solutions:

a multi-tube biofilter system for treating waste gas, comprising a multi-tube biofilter and a nutrient solution supply system, wherein said multi-tube biofilter comprises an outer casing, at least two reticulated tubes disposed in the outer casing, a packing medium portion, and a nutrient solution spraying system; wherein the outer casing is opened to define a gas inlet, a gas outlet, and a water outlet therein; wherein the packing medium portion is attached to the outer surfaces of the reticulated tubes; additionally, a liquid entering end of the nutrient solution spraying system is in communication with the nutrient solution supply system via a pipeline, and a solution spraying end of the nutrient solution spraying system faces the reticulated tubes.

The further improvements of the present invention are as follows:

The outer casing is vertically arranged, the gas inlet is provided on the bottom of the outer casing, the gas outlet is provided on the top of the outer casing, and the nutrient solution spraying system is provided over the reticulated tubes and the solution spraying end faces terminal portions of the reticulated tubes.

The outer casing is horizontally arranged, the nutrient solution spraying system is provided over the reticulated tubes, and the solution spraying end faces outer lateral walls of the reticulated tubes.

One end of each of the reticulated tubes is coupled with a gas entering channel communicatively connected to the gas inlet; another end of the reticulated tube is closed and a second gas channel is defined between every two neighboring the reticulated tubes.

At least two gas distributing tubes are provided between the gas entering channel and the gas inlet; each of the gas distributing tubes comprises a gas control valve provided thereat.

Each of the reticulated tubes has a range of length from 0.3 m to 5 m.

The gas inlet of the outer casing is coupled with a waste gas supply system via a preprocessing system, and the preprocessing assembly comprises a dust collector and a humidifier connected in sequence.

The nutrient solution supply system comprises a nutrient solution storage reservoir, a nutrient solution supply pump, and a timer; wherein the nutrient solution supply pump is provided in the nutrient solution storage reservoir, and the nutrient solution supply pump has an output end communicatively connected to the nutrient solution spraying system via a first pipeline and a control end connected to the timer.

The nutrient solution storage reservoir is communicatively coupled with the water outlet via a second pipeline.

Each of the reticulated tubes and the packing medium portion has a ring-shaped, waving ring-shaped, or folded ring-shaped cross section.

Compared to the prior art, the present invention has the following advantages:

The present invention, by providing at least two reticulated tubes provided in the outer casing, wherein the reticulated tubes have wrapped on their outer surface a cylindrical packing medium layer, whereby the gas flow from inside to outside or vice versa; is scientific in design, reasonable in structure, and has good performance of gas distribution such that the present invention is accommodated to characteristics of degradation of microorganisms of malodorous gas or low concentration volatile organic compounds.

2. The present invention employs reticulated tubes as its support structure and arrangement, and has the following advantages:

(1) It greatly increases surface area per unit volume of the packing medium portion in the reactor such that more types of packing medium materials can be used; the filter of the present invention employs a support structure comprising a plurality of reticulated tubes that not only fasten a porous integral circular packing medium layer on an outer lateral wall of each of reticulated tubes, but also make the packing medium portion wrap on each of the reticulated tubes; wherein the packing medium portion is heaped into by spherical shaped, square-shaped or rectangle-shaped porous packing medium having a certain size and simply disposed; and to also design the ring-shaped packing medium portion as a ring body enclosed from simple, wave-shaped or fold over material, wherein the surface area per unit volume of the packing medium portion in the reactor of the present invention is increased, and more types of packing medium materials can be used for the filter of the present invention, compared to the heaped packing medium used in the conventional biofilter and the thin layer of packing medium employed in the tube gas biological filter;

(2) The present invention employs a support structure comprising a plurality of reticulated tubes which reduces the footprint thereof. According to the volume of the gas to be processed, the number and size of the reticulated tubes used for supporting the packing medium portion can be arranged as desired to overcome the disadvantages of size limitation and low capacity utilization rate of the tube gas biological filter which greatly reduce the footprint;

(3) The reticulated tubes are evenly arranged to make full use of the nutrient solution. As the plurality of reticulated tubes are evenly staggered in the biofilter, the nutrient solution spraying nozzle provided in an upper end of the filter can evenly spray the nutrient solution to the packing medium portion, wherein the vertical type of filter allows the nutrient solution to flow from the top to the bottom along the ring-shaped packing medium portion such that the nutrients can be gradually absorbed. For a horizontal type of filter, the nutrient solution flows from the packing medium layer above the upper reticulated tubes to the packing medium layer below the lower reticulated tubes and the nutrients can be gradually absorbed such that the nutrients from the nutrient solution can be fully absorbed and retain high bioactivity of microorganisms for a long period of time so as to ensure a stable treatment effect;

3. During the period the gas enters, the present invention carries out a second gas distribution such that the present invention is easy to control, has good performance of gas distribution, and strong resistance capacity to shock load. At least two reticulated tubes are evenly arranged in the filter and each of the reticulated tubes has an upper opening in communication with one of the gas distributing tubes. Each of the gas distributing tubes comprises a gas control valve. Accordingly, the waste gas from the waste gas supply device is divided into at least two gas flows, each of which enter into the corresponding reticulated tubes and complete the first gas distribution. The operation of the first gas distribution is easy to control and results in even gas distributions. After this step, the waste gas enters into the reticulated tubes and a second gas distribution of the waste gas is created, wherein the increased surface area per unit volume of the packing medium portion in the reactor of the present invention greatly reduces speed of gas flows passing through the packing medium portion and makes the gas distribution more reasonable. In addition, the fluctuation of amount of gas can be simultaneously shared by a plurality of gas distributing tubes.

Moreover, the relative high fluctuation of amount of pollutants in the waste gas can be simultaneously shared by a plurality of waste gas flows such that the present invention has a very strong resistance capability to shock load.

4. The present invention has advantages of short residence time, high removal efficiency, and stable performance over a long-term operation. For the ring-shaped packing medium block wrapped on the surface of the outer lateral wall of each of the reticulated tubes is relatively thin (2 to 40 cm), the waste gas has a short passing time (the residence time is only 1 to 60 seconds), and the drop of pressure is small. According to the mechanism of the biofilter used to treat the waste gas, most of pollutants in the waste gas are bio-degraded on the surface of the medium, and because of the increased surface area per unit volume of the packing medium portion in the reactor the contact areas among three phases of gas, liquid and biofilms are greatly increased such that the present invention has a removal efficiency of up to 85%-99%. After the waste gas is exhausted from one of the reticulated tubes through the packing medium portion, the un-degraded pollutants in the waste gas can come into contact with outer surfaces of other reticulated tubes or biofilms in the other reticulated tubes to create a second contact or multiple contacts to additionally degrade the un-degraded pollutants so as to ensure a high and stable decontamination efficiency. In addition, because the plurality of ring-shaped packing medium portions are evenly arranged in the filter, the predominant organism groups can easily develop in the packing medium portions by spraying the circulating nutrient solution and the disruption caused by the waste gas to ensures the stable performance over a long-term operation.

5. The present invention is simple to maintenance, easy to operate, and has a long-term cycle of operation. Since each of reticulated tubes provided in the multi-tube biofilter system are relatively independent and the gas control valves are respectively provided at the gas distributing tubes, such that when a reticulated tube or the packing medium wrapped on the reticulated tube is damaged, it is easy to remove or replace. Additionally, a plurality of nutrient solution nozzles provided at an upper end of the biofilter systems can prevent dead corners of spray to provide periodically sufficient nutrients for each of biofilms provided in the packing medium wrapped on the reticulated tubes, and wash over excess biofilms on the packing medium to effectively control the amount of microorganisms and avoid clogging.

6. The present invention has several advantages such as; low cost of operation, compact structure, and small footprint.

These and other objectives, features, and advantages of the present invention will become apparent from the following detailed description, the accompanying drawings, and the appended claims.

DETAILED DESCRIPTION OF THE PREFERRED EMBODIMENT

Figure 1:
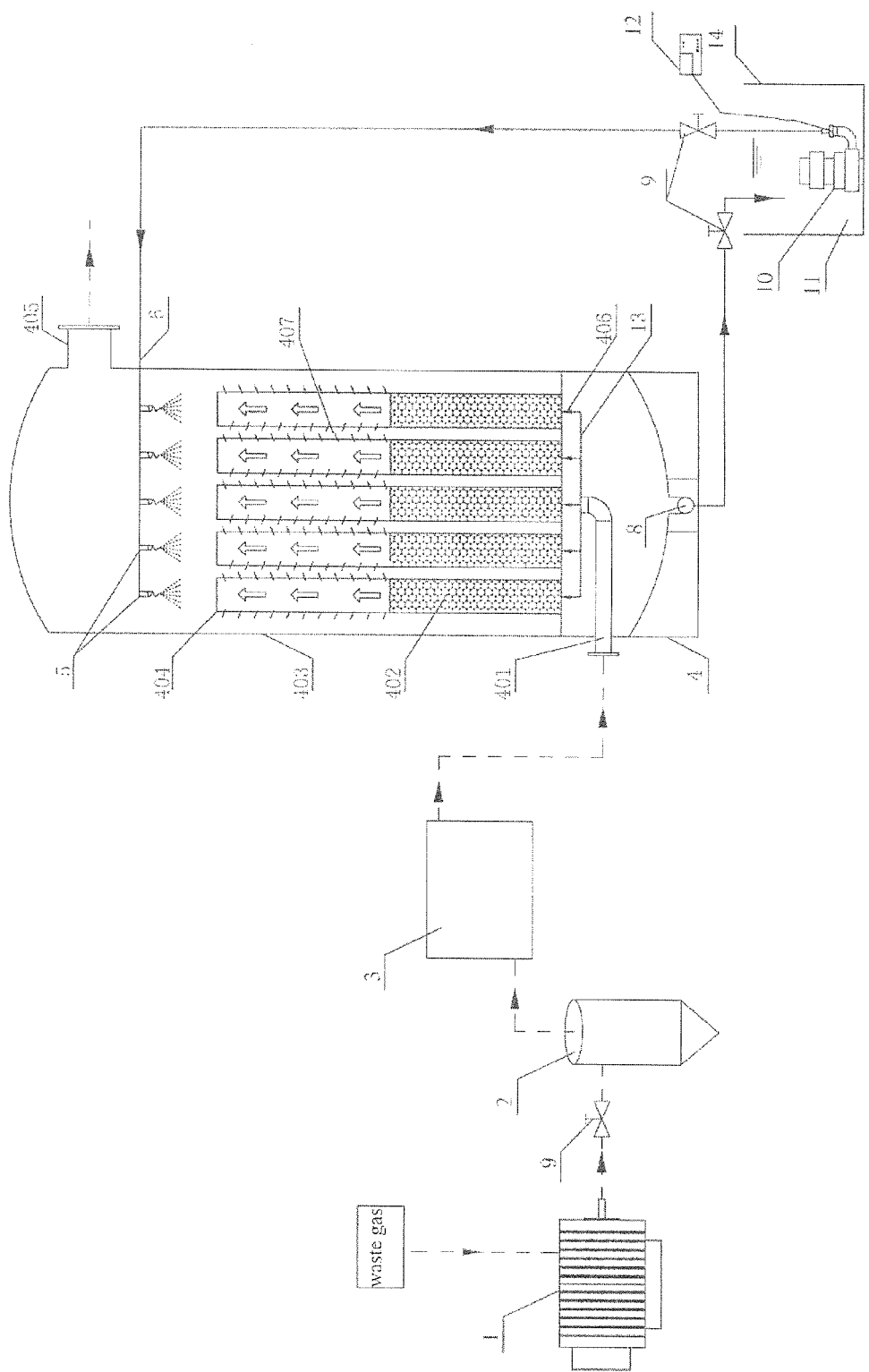
FIG. 1 is a structure diagram of an example according to the first preferred embodiment of the present invention.
Figure 2:
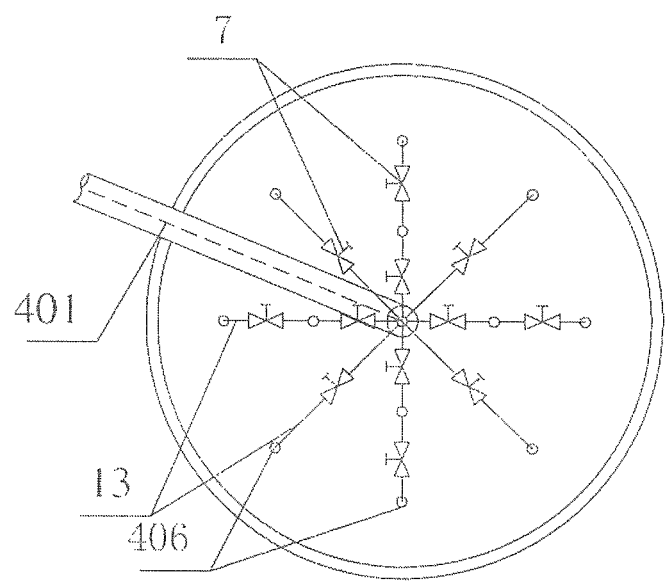
FIG. 2 is a structure and principle diagram of the gas entering end of the reticulated tube according to the above first preferred embodiment of the present invention.
Figure 3:
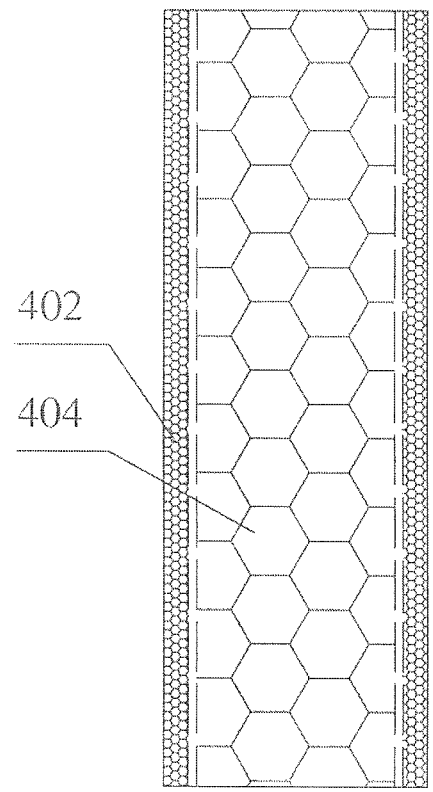
FIG. 3 is a front view of the cooperation between each of reticulated tubes and the packing medium portion according to the above first preferred embodiment of the present invention.
Figure 4:
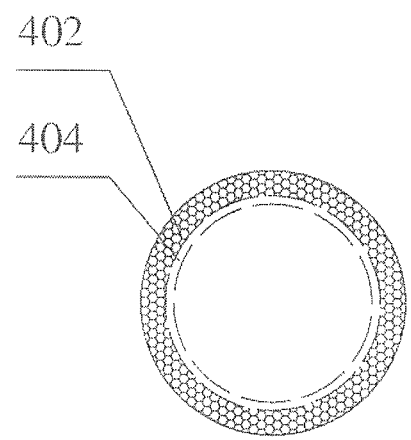
FIG. 4 is a top view of the cooperation between each of reticulated tubes and the packing medium portion according to the above first preferred embodiment of the present invention.

The following description is disclosed to enable any person skilled in the art to make and use the present invention. Preferable embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to the drawings and the embodiments, the present invention is further described in detail as follows.

The first preferred embodiment, as shown in FIG. 1, FIG. 2, FIG. 3 and FIG. 4, is a multi-tube biofilter system for treating waste gas, wherein the multi-tube biofilter system comprises a multi-tube biofilter 4 and a nutrient solution supply system 14. The multi-tube biofilter 4 further comprises an outer casing 403, at least two reticulated tubes 404 provided in the outer casing 403, the packing medium portion 402, and a nutrient solution spraying system. The outer casing 403 is rectangular or round shape, and the outer casing 403 is opened to define a gas inlet 401, a gas outlet 405, and a water outlet 8. The purified gas is exhausted through the gas outlet 405, and the sprayed nutrient solution is exhausted through the water outlet 8 or recycled back to the nutrient solution supply system 14 for being reused. At least two reticulated tubes 404 are evenly arranged in the outer casing 403, and the packing medium portion 402 is attached to an outer surface of each of reticulated tube. Each of the reticulated tubes 404 is a gas entering tube made of corrosion-resistant material which has a reticulated outer lateral wall and a closed upper end, wherein the gas entering tube is convenient to remove or replace. The gas entering tube has a height of 0.3 m-5 m. The reticulated tubes 404 are also used as a support structure for the packing medium portion 402. The packing medium portion 402 is a ring-shaped packing medium layer, which contains a kind of packing medium portion inoculated with microorganisms, wherein the packing medium portion 402 employs a filtering medium made of evenly porous integral material or a packing medium layer heaped randomly into by spherical shaped, square-shaped or rectangle-shaped porous packing medium material having a certain size. The porous packing medium material has a porosity of over 90%, a percentage of opening of over 95%, a pore size of 1 mm-5 mm, a tensile strength of over 5000 Pa and a specific surface area of 150 m2/m3-1000 m2/m3. The microbial carrier material of the biofilms of the packing medium portion 402 can be a porous material, such as mesh sponge, porous ceramic, or molding diatomite; wherein the multi-tube biofilter 4 is inoculated with microorganisms in the packing medium before the present invention is started or if necessary. The microorganisms inoculated are a specific microbial strain or residual activated sludge from a sewage treatment plant. Each of reticulated tubes 404 and the packing medium portion 402 each has a ring-shaped, waving ring-shaped or folded ring-shaped cross section.

In this preferred embodiment, the nutrient solution supply system 14 comprises a nutrient solution storage reservoir 11, a nutrient solution supply pump 10 and a timer 12. The nutrient solution supply pump 10, which is provided in the nutrient solution storage reservoir 11, has an output end connected to the nutrient solution spraying system via a pipeline, as well as a control end connected to the timer 12 to supply intermittently the nutrient solution in a fixed quantity. The nutrient solution storage reservoir 11 is communicatively coupled with the water outlet 8 via a pipeline. A liquid entering the end of the nutrient solution spraying system is in communication with the nutrient solution supply system 14 via a pipeline, and a solution spraying end of the nutrient solution spraying system faces the reticulated tubes 404. The nutrient solution spraying system comprises a nutrient solution tube 6 communicatively connected to the nutrient solution spraying system 14, and a plurality of nutrient solution spraying nozzles 5 provided at the nutrient solution tube 6.

Each water exhaust tube is communicatively coupled with the water outlet 8 and the nutrient solution tube 6 is coupled with a liquid control valve 9. Each of the nutrient solution nozzles 5 spray the nutrient solution to the packing medium portion 402 so predetermined level of moisture is maintained in the packing medium portion 402. The nutrient solution also supply essential nutrients for microorganisms in the filter of the present invention, and wash over excess microorganisms in the packing medium portion 402 to avoid blockage.

One end of each of the reticulated tube 404 is coupled with a gas entering channel 401 communicatively connected to the gas inlet 406. Another end of the reticulated tube 404 is closed and a second gas channel 407 is defined between every two neighboring reticulated tubes 404.

At least two gas distributing tubes 13 are provided between the gas entering channel 406 and the gas inlet 401. A gas control valve 7 is provided at each of the gas distributing tubes 13. The waste gas from the waste gas supply system 1 is evenly distributed into a gas entering channel 406 provided at a bottom of each of the reticulated tubes 404 and then radially enters into the ring-shaped packing medium portion 402 in a radial direction via the reticulated tubes 404. The waste gas may also enter into the reticulated tubes 404 from the outside of the reticulated tubes 404 to the inside of the reticulated tubes 404 in a radial direction passing through the ring-shaped packing medium portion 402, wherein the pollutants in the waste gas are degraded in the ring-shaped packing medium portion 402 which generate the metabolic products including $CO_2$ and $H_2O$, the remaining metabolic products are used by microorganisms for anabolism and increasing the biomass of the microorganisms. Each of the reticulated tubes 404 has a length of 0.3 m to 5 m.

The gas inlet 401 of the outer casing 403 is coupled with a waste gas supply system 1 via a preprocessing system, wherein the preprocessing system comprises a dust collector 2 and a humidifier 3 connected in sequence. The dust collector 2 has an entering opening communicatively coupled with the outlet of the waste gas supply system 1 and an exhausting opening communicatively coupled with an entering opening of the humidifier 3. The humidifier 3 has an exhausting opening communicatively coupled with the gas inlet 401 provided at the bottom of the multi-tube biofilter 4 such that the waste gas containing VOCs or malodorous gases are pretreated to remove dust and humidify, and then the waste gas enters into the multi-tube biofilter 4 and is treated.

The outer casing 403 is vertically arranged, and houses the gas inlet in the bottom of the outer casing 403. The gas outlet 405 is provided in the top of the outer casing 403, the nutrient solution spraying system is provided over the reticulated tubes 404, and the solution spraying end faces terminal portions of the reticulated tubes 404.

Referring to the Table 1, the present invention has the following advantages: good performance of gas distribution, strong resistance capability to shock load, small drop of pressure, the packing medium portion which is difficult to clog, low cost of construction and operation, and stable performance over a long-term operation. Table 1 compares the present invention to existing filtering technology for treating waste gases which contain malodorous gases and low concentrations of VOCs.

TABLE 1

|  | Conventional biological filter | Biological trickling filter | Multi-tube biofilter system of the present invention |
|---|---|---|---|
| Height of bed layer (m) | 1~2 | 0.8~1.5 | 0.10~0.40 |
| Initial porosity of bed layer | 20% | 50% | >90% |
| Packing medium | Compost, gravel, etc | Compost, gravel, synthetic material, etc | Synthetic porous material |
| Working life of packing medium (year) | 1~4 | 2~6 | >5 |
| Residence time of waste gas (s) | 60~300 | 30~120 | 2~50 |
| Load of Volume capability ($m^3/m^3/d$) | 1000 | 5000 | 20000 |
| Ability of treatment capacity | smaller | larger | Large |
| Added liquid and amount | Water, less | Nutrient solution, more | Nutrient solution, more |
| Controllability of processing | Difficult | easier | Easy |
| Stability of processing | Unstable | more stable | Stable |
| Applicable scope | Narrower | Wide | Wide |
| Removal efficiency | Common | Higher | High |
| Construction Cost | Low | Higher | Lower |
| Footprint | Very large | smaller | small |
| Cost of operation and maintenance | Low | Common | Lower |

The operating principle of the present invention is that: the waste gas, containing malodorous gases and low concentration of VOCs, supplied by the waste gas supply system 1 first enters into the dust collector 2. The waste gas then enters into the humidifier 3 via a pipeline and is humidified. After the waste gas is preprocessed, the waste gas then enters into the gas inlet 401 of the multi-tube biofilter 4, and then enters into the reticulated tubes 404, which are provided evenly in the multi-tube biofilter 4, through the gas distributing tubes 13. Therefore, when flowing upwards in the reticulated tubes 404, the waste gas radially enters into the ring-shaped packing medium portion 402 via the reticulated tubes 404. Alternatively, the waste gas can enter into the reticulated tubes 404 from the outside of the reticulated tubes 404 to the inside of the reticulated tubes 404 at a radial direction passing through the ring-shaped packing medium portion 402 and the pollutants in the waste gas come into contact with the ring-shaped packing medium portion 402. The pollutants in the waste gas are degraded in the ring-shaped packing medium portion 402 and generate $CO_2$, $H_2O$, and new cells; wherein the purified waste gas is exhausted through the gas outlet 405 provided at an upper end of the multi-tube biofilter 4. Each of the nutrient solution spraying nozzles 5 provided at the upper end of the multi-tube biofilter 4 is communicatively coupled with the nutrient solution storage reservoir 11 and the nutrient solution supply pump 10 via a nutrient solution tube 6. The nutrient solution spraying nozzles 5 are controlled by the timer 12 to supply timely and intermittently the nutrient solution for the packing medium portion 402. The nutrient solution and the waste gas flow in opposite directions in the multi-tube biofilter 4; wherein the nutrient solution is exhausted through the water outlet 8 provided at the bottom of the multi-tube biofilter 4. When the biomass carried in one of the reticulated tubes 404 or the packing medium wrapped on the reticulated tube 404 is excessive, the reticulated tube 404 or the packing medium portion 402 wrapped on the reticulated tube 404 need to be cleaned or replaced to maintain normal, stable, and efficient operation of the biofilter systems.

Figure 5:
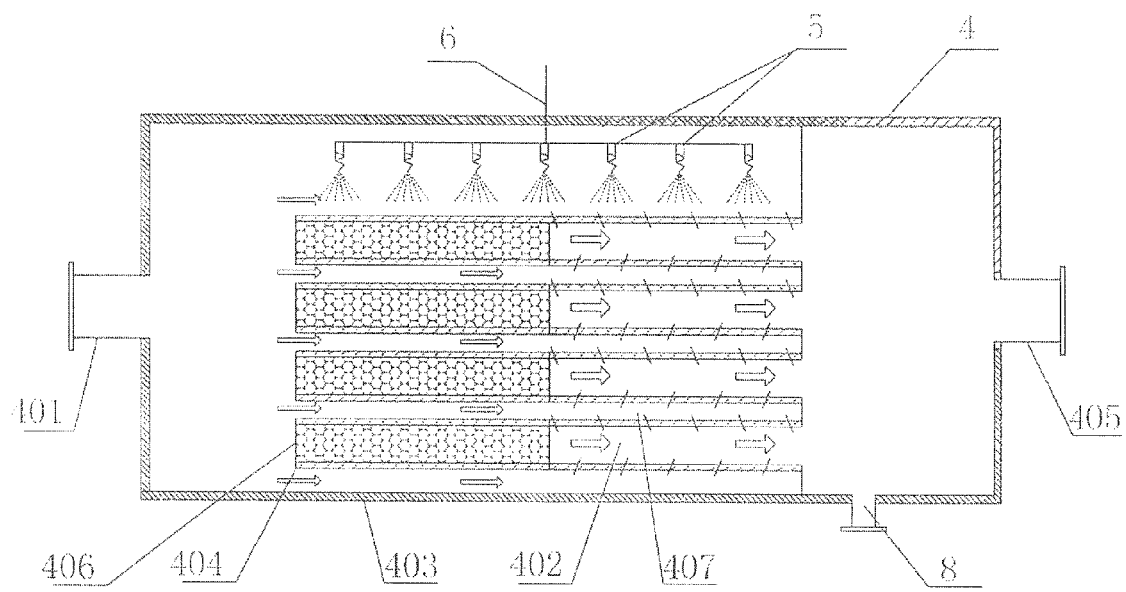
FIG. 5 is a structure diagram of the multi-tube biofilter according to the second preferred embodiment of the present invention.
Figure 6:
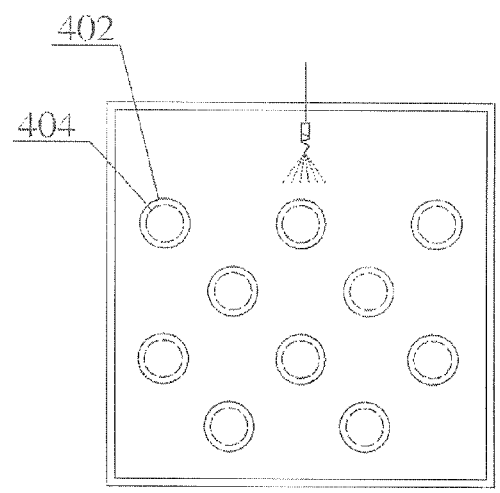
FIG. 6 is a schematic diagram of spraying reticulated tubes according to the above second preferred embodiment of the present invention.

The second preferred embodiment as shown in FIG. 5 and FIG. 6, the outer casing 403 can be horizontally arranged, and the nutrient solution spraying system is provided over the reticulated tubes 404, wherein the spraying ends face the outer lateral walls of the reticulated tubes 404 to adapt for different work situations according to the principle of most optimal design. The other structures in the second preferred embodiment and the operating principle are fundamentally the same as the first preferred embodiment.

The above is only the preferred embodiment of the present invention and the scope of the present invention is not limited by the above embodiments; therefore, all of the technical solutions within the spirit of the present invention should be included within the scope of the present invention. It should be point out that this invention includes all modifications encompassed within the spirit and scope of the present invention; for one skilled in the art.

What is claimed is:

1. A multi-tube biofilter system for treating waste gas, comprising:
    a nutrient solution supply system;
    a multi-tube biofilter which comprises:
    an outer casing having a gas inlet for guiding waste gas to enter into said outer casing, a gas outlet, and a water outlet;
    at least two reticulated tubes spacedly disposed in said outer casing to form a second gas channel between every two neighboring said reticulated tubes, wherein each of said reticulated tubes has a first closed end extended toward said gas outlet of said outer casing and an opposed second end communicatively linked to said gas inlet for allowing the waste gas radially flowing into and away from said reticulated tube;
    a packing medium portion attached to an outer surface of each of said reticulated tubes at said second end thereof for contacting with the waste gas when the waste gas flows in a radial direction of said reticulated tube so as to degrade pollutants in the waste gas;
    a nutrient solution spraying system having a liquid entering end communicatively linked to said nutrient solution supply system and a plurality of nutrient solution spraying nozzles aligned with said reticulated tubes respectively for supplying nutrient solution to said packing medium portion at each of said reticulated tubes; and
    a distributing tube communicatively coupled with said gas inlet with said second end of each of said reticulated tubes, and a gas control valve provided at each of said distributing tubes for distributing the waste gas to each of said reticulated tubes through said distributing tube in a controlling manner; and
    a preprocessing system and a waste gas supply system operatively linked to said gas inlet of said outer casing via said preprocessing system, wherein said preprocessing system comprises a dust collector and a humidifier connected each other in sequence for removing dust and humidify of the waste gas before entering into said multi-tube biofilter, wherein said nutrient solution spraying system and said gas inlet guide the nutrient solution and the waste gas respectively to flow in opposite directions in said multi-tube biofilter, wherein said nutrient solution supply system comprises a nutrient solution storage reservoir, a nutrient solution supply pump and a timer, wherein said nutrient solution supply pump is provided in said nutrient solution storage reservoir, and said nutrient solution supply pump has an output end connected to said nutrient solution spraying system and a control end connected to said timer for intermittently supplying the nutrient solution to said packing medium portion at each of said reticulated tubes.

2. The multi-tube biofilter system, as recited in claim 1, wherein said nutrient solution storage reservoir is operatively linked to said water outlet of said outer casing.

3. The multi-tube biofilter system, as recited in claim 2, wherein a cross section of each of said reticulated tubes and said packing medium portion is selected from the group consisting of ring-shape, waving ring-shape and folded ring-shape.

4. The multi-tube biofilter system, as recited in claim 3, wherein said outer casing is orientated vertically at a position that said gas inlet is formed at a bottom of said outer casing while said gas outlet is formed at a top portion of said outer casing, wherein said reticulated tubes vertically disposed in said outer casing at a position that said nutrient solution spraying nozzles are aligned with and over said closed ends of said reticulated tubes respectively.

5. The multi-tube biofilter system, as recited in claim 4, wherein said outer casing is orientated horizontally at a position that said gas inlet and said gas outlet are formed at two side portions of said outer casing respectively, wherein said reticulated tubes horizontally disposed in said outer casing at a position that said nutrient solution spraying nozzles are provided over said reticulated tubes respectively to face outer lateral walls of said reticulated tubes.

6. The multi-tube biofilter system, as recited in claim 4, wherein each of said reticulated tubes, having a length of 0.3 m-5 m, is replaceable in said outer casing.

7. The multi-tube biofilter system, as recited in claim 5, wherein each of said reticulated tubes, having a length of 0.3 m-5 m, is replaceable in said outer casing.

* * * * *